United States Patent [19]
Wong

[11] Patent Number: 4,928,703
[45] Date of Patent: May 29, 1990

[54] NON-CONTACT RESPIRATION RATE AND APNEA MONITOR USING PULMONARY GAS EXCHANGE TECHNIQUE

[75] Inventor: Jacob Y. Wong, Santa Barbara, Calif.

[73] Assignee: Evionics, Inc., Santa Barbara, Calif.

[21] Appl. No.: 275,762

[22] Filed: Nov. 23, 1988

[51] Int. Cl.$^5$ .............................................. A61B 5/08
[52] U.S. Cl. ................................ 128/719; 128/664; 128/716
[58] Field of Search ............... 128/633, 719, 663.01, 128/664, 632, 665; 340/573, 575; 250/338.1, 339–343, 394, 338.4, 338.5; 356/51, 436, 437, 440

[56] References Cited

U.S. PATENT DOCUMENTS

| | | | |
|---|---|---|---|
| 4,350,166 | 9/1982 | Mobarry | 128/719 |
| 4,423,739 | 1/1984 | Passaro et al. | 128/633 |
| 4,578,762 | 3/1986 | Wong | 128/719 |
| 4,648,396 | 3/1987 | Raemer | 128/719 |
| 4,709,150 | 11/1987 | Burough et al. | 250/338.1 |
| 4,730,112 | 3/1988 | Wong | 250/343 |
| 4,738,266 | 4/1988 | Thatcher | 128/719 |
| 4,800,886 | 1/1989 | Nestor | 128/664 |
| 4,827,938 | 5/1989 | Parker | 128/664 |
| 4,829,535 | 5/1989 | Utaka | 372/20 |

*Primary Examiner*—Randall L. Green
*Assistant Examiner*—K. M. Reichle
*Attorney, Agent, or Firm*—Daniel C. McKown

[57] ABSTRACT

An apnea detector uses an active pulsed source of radiation to monitor the respiration of a patient. Radiation from the source is formed into a collimated beam that is directed through the space into which the patient is breathing. The exhaled gases contain a smaller concentration of oxygen and a larger concentration of carbon dioxide compared with the atmosphere. Each exhalation of the patient produces a small cloud of the exhaled gases, which rapidly diffuse and disperse. Corresponding to the appearance and disappearance of these clouds of gas, the transmission of the collimated beam will vary in step with the patient's breathing. The fluctuations in the transmitted radiation are analyzed by a signal processor which generates an alarm signal when either the magnitude or the frequency of these fluctuations falls outside of preset limits. Either carbon dioxide or oxygen may be monitored as the absorbing gas.

10 Claims, 4 Drawing Sheets

NON-CONTACT RESPIRATION RATE AND APNEA MONITOR USING PULMONARY GAS EXCHANGE TECHNIQUE

BACKGROUND OF THE INVENTION

1. Field of the Invention

The present invention is in the field of medical instrumentation. More specifically it relates to improved respiration rate and apnea monitor.

2. The Prior Art

Periods of cessation of breathing or apneic periods have long been recognized as a potential source for morbidity and mortality in both infant and adult patients. Also, many drugs may alter respiration activity as will certain types of trauma and illness. In addition, patients with artificial airways are not totally immune from ventilator detachment or various forms of airway obstruction. Thus it is evident that an accurate and reliable respiration rate and apnea monitor would greatly improve patient care.

In certain instances, such as the sudden infant death syndrome (SIDS) and acute adult sleep disorders, the timely detection of apneic episodes and subsequent corrective intervention often means the difference between life and death. Currently available apnea monitors can generally be classified into three basic types.

The first type is an indirect monitor which senses ventilatory effort or body movement and change in heart rate. This type of indirect monitor is not completely reliable and can give a false indication of continued breathing when actual breathing has stopped. This is because many apneic episodes consist of spontaneous upper airway obstruction in which continuing breathing or ventilatory effort fails to produce air flow. For example, if the infant has stopped breathing due to a blockage of the breathing passageways, and the chest of the infant continues to heave in a spasmotic effort to reestablish breathing, a false sense of continued breathing will be recorded by such motion sensing devices.

The second type of respiration rate/apnea monitors actually senses the flow of exhalation with the use of an appropriately placed flow sensor. Even this type of monitor is not totally immune from false indication of breathing as air flow does not automatically guarantee actual breathing by the patient—such air exchanges might never reach the patient's lungs.

The third type of respiration rate/apnea monitors respond directly to pulmonary gas exchange instead of just ventilatory effort or physical air flow. Carbon dioxide has long been recognized as the most reliable method for monitoring respiratory activity. The principle of operation of this device type is optical sensing (infrared absorption) of exhaled $CO_2$.

Some types of respiration rate/apnea monitors require attachment to the patient. While these attachments constitute a measure of discomfort and inconvenience, they are tolerable in most instances due to the lack of anything better. However, there exist other situations where such attachments are serious impediments to the well-being of the patient under medical care. Examples are very small infants, where often the attachments are in the way of other more acutely needed and life-saving apparatus. Furthermore, due to the small size of some of these patients, these attachments can no longer be guaranteed to work properly and their effectiveness as respiration rate/apnea monitors is seriously undermined. For cases where the respiration rate/apnea monitors are employed to prevent crib deaths and adult sleep disorders these attachments may introduce undesirable side-effects in that the subjects are rendered so uncomfortable that they simply cannot sleep normally.

Attempts had been made in the past to devise instruments for non-contact apnea detection. In U.S. Pat. No. 4,350,166, Mobarry proposed the idea of a non-contacting apnea detector which utilizes a long wave infrared detecting device arranged with a focusing means to define a predetermined field of view. This detector is positioned to include the infant or at least the head and shoulder portion of the infant in that field of view. The exhalations of the infant include large quantities of $CO_2$. Carbon dioxide is absorbent to the long wave infrared radiation. The detector detects the fluctuations in the infrared radiation due to the absorption caused by the exhalations of the infant. The resulting signal is applied to a suitable alarm circuit to indicate an interruption of the exhalation exceeding a predetermined time interval.

Unfortunately, such a non-contacting apnea monitor suffers from an acute lack of sensitivity. As is evident from the U.S. Pat. No. 4,350,166 the area of interest, namely the mouth and nose portion of the infant's head, constitutes only a small fraction of the total field of view subtended at the detector. Consequently, the small modulation of the radiation seen by the detector due to the $CO_2$ exhalation from the infant's mouth or nose is hardly discernible from other changes unrelated to the infant's breathing. These other changes include those originating in the detector system (extraneous noises) and those originating in the background (such as changes in temperature and/or emissivity of objects, or motion of background objects). Because of this major drawback, no apnea monitor of this design is currently on the market.

SUMMARY OF THE INVENTION

It is an object of the present invention to provide an improved respiration rate/apnea monitor which overcomes most or all of the shortcomings of the currently available instruments.

It is a further object of the present invention to provide a workable non-contact apnea detector which overcomes the inadequacies of previously proposed devices.

Mobarry's system, referred to above, makes use of the long wavelength thermal radiation which all objects emit continuously and without external stimulation. Such sources of radiation are sometimes called passive sources. At the ambient temperatures involved in detecting apnea, the problems of passive sources are many. They are not bright sources, and typically the sources are of large area, which makes it impossible from a practical standpoint to focus their radiation into a beam or to modulate the radiation intentionally for aiding identification or detection. Further, since the wavelength and brightness of the emitted radiation are dependent on temperature and emissivity, and since all of the objects are near room temperature, contrast between the object being detected and the background is very low. Such radiation is not controllable in the sense that it cannot be turned on or off at will, its wavelength may not be appropriate, and its brightness cannot be increased.

In contrast, the present invention uses a source that emits radiation over and above its room-temperature thermal radiation. Such a source is sometimes called an active source in contrast to the passive source described in the previous paragraph. A source having a particular wavelength may be chosen, and the brightness of the source may be controlled. The source may be modulated. Its size can be chosen to facilitate formation of a beam. These features can be used to permit radiation from such a source to be identified and distinguished from the background radiation. Appropriate calculations bear out that an active source is far superior for use in an apnea detector, and the use of an active source results in greatly improved performance over that obtainable with a passive source.

Nor is safety of the patient a problem. The radiation used in the present invention achieves its superior result not by brute force intensity, but by the subtle techniques of optical filtering at the wavelength of the radiation and of electronic filtering at the frequency at which the source is modulated. These techniques obviate the need for using dangerously high power levels.

In accordance with the present invention, an active infrared source is provided, which is controllable and capable of being modulated. Radiation from this source is formed into a beam that is directed through the space into which the patient is breathing. Each cloud of breath includes a greater concentration of $CO_2$ than the ambient air, causing the beam to be more strongly absorbed until the cloud disperses. The resulting sequence of variations in the intensity of the beam is analyzed to determine whether the time between successive breaths is excessive and to determine whether the amplitude of the variations is adequate. If either the frequency or the amplitude criterion is not met, an alarm signal is produced.

Before the present invention, it was generally thought that the most reliable method of monitoring respiration rate/apnea activity was the detection of exhaled $CO_2$ from a patient. Because $CO_2$ has two prominent absorption bands in the middle infrared region of the electromagnetic spectrum, namely around 2.7 and 4.26 microns, standard nondispersive infrared (NDIR) techniques using an incoherent broadband source can readily be used to detect the changing $CO_2$ concentrations from the exhalation of the patient as a result of breathing.

The system of the present invention greatly improves $CO_2$ modulation sensitivity because the area where $CO_2$ modulation takes place now occupies a major portion of the field of view as seen by the detector.

Furthermore, unlike the method proposed by Mobarry (U.S. Pat. No. 4,350,166) the currently proposed arrangement can take advantage of the synchronous detection technique for rejecting ambient background noise with the use of a mechanical chopper or equivalent placed in front of the infrared source, or by electrically modulating a laser diode source. The frequency of modulation is much higher than the respiration rate.

As mentioned earlier, incoherent IR sources are relatively large physically and are therefore difficult to collimate. On the other hand, very intense incoherent IR sources are readily available. The advent of IR transmitting fibers is therefore utilized to advantage in one embodiment of the present invention. Infrared radiation is first coupled into an IR transmitting fiber of very small core size (0.1-1.0 mm diameter typical) and the radiation emerging from the other end of the fiber appears to come from a point source. The coupling efficiency is generally rather small; but since the IR source itself can be made to be as intense as one desires (tens of watts typical) the final result is that one can have a reasonably incoherent IR source whose radiation can be well collimated for use in the proposed improved respiration rate/apnea monitor optical arrangement.

In the preferred embodiment, a coherent IR source, namely an infrared laser, is used. Currently, no practical lasers are readily available in the mid-infrared region where $CO_2$ has two of its most prominent absorption bands. However, the advent of semiconductor lasers for use in the telecommunication industry permits some of these same devices to be used for the detection of $CO_2$ and other gases, albeit in a different spectral region. For example, in addition to the two absorption bands in the mid-infrared region, $CO_2$ also has a fairly strong absorption band at 1.58 microns. One of the commonly used telecommunication semiconductor lasers, namely the 1.55 micron InGaAsP laser diode, can be used (with a slight shift in the lasing wavelength) as a coherent IR source for the detection of $CO_2$. The appropriate detector would be a germanium photodiode or a InGaAsP photodiode.

Although all current respiration rate/apnea monitors utilizing the pulmonary gas exchange technique use the difference between the inhale (0%) and exhale (5%) $CO_2$ concentration as a means for breath detection, the present inventor recognized that the same can be applied to the other pulmonary exchange gas, namely oxygen. In the latter case the inhale oxygen concentration (20.6%) is normally greater than the exhale concentration (16%), a situation which is opposite to that of $CO_2$ where the exhale level (5%) is greater than the inhale level (0%). To date, no one has used oxygen in the design of pulmonary gas exchange respiration rate/apnea monitors, because fast oxygen sensors capable of measuring oxygen concentration level in much less than a second (0-90%) are not readily available. The most common types of oxygen sensors operate on an electrochemical principle, in either the polarographic or the galvanic mode. Oxygen sensors using either of these approaches have typical response times (0-90%) of tens of seconds. They are therefore too slow to be used in the respiration rate/apnea monitors. Oxygen sensors using thermoconductivity methods suffer a similar fate as the electrochemical types in having too slow a response time. Fast oxygen sensors do exist. They use either a paramagnetic (Pauling) method or a modified electrochemical technique that employs a very high temperature electrolyte. These sensors are very complex and expensive and they do not lend themselves well to the current application.

The preferred embodiment of the present invention takes advantage of the recently proposed method of oxygen detection using visible radiation (Wong in U.S. Pat. 4,730,112) and the readily available 762 nm AlGaAs laser diodes brought about by the rapidly advancing device technology of the telecommunication and the commercial compact disc player (CD) industries. The use of oxygen level fluctuations as a means of detecting breathing is superior to the use of its counterpart, namely $CO_2$, due to the extreme specificity of the oxygen absorption at around 762 nm (U.S. Pat. No. 4,730,112) and hence the ease of detection free from any potential interferences. Furthermore, the detector usually used for detecting the 762 nm radiation from the AlGaAs laser diode, namely the Si photodiode, has a much higher detectivity than the room-temperature-operating IR detectors (e.g., PbSe photoconductor or pyroelectric detectors). The technical and commercial maturity of both the AlGaAs laser diodes as coherent sources and the Si photodiodes as detectors renders the use of oxygen detection for respiration rate/apnea monitors a much more efficacious and economical approach than the use of the $CO_2$ gas.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
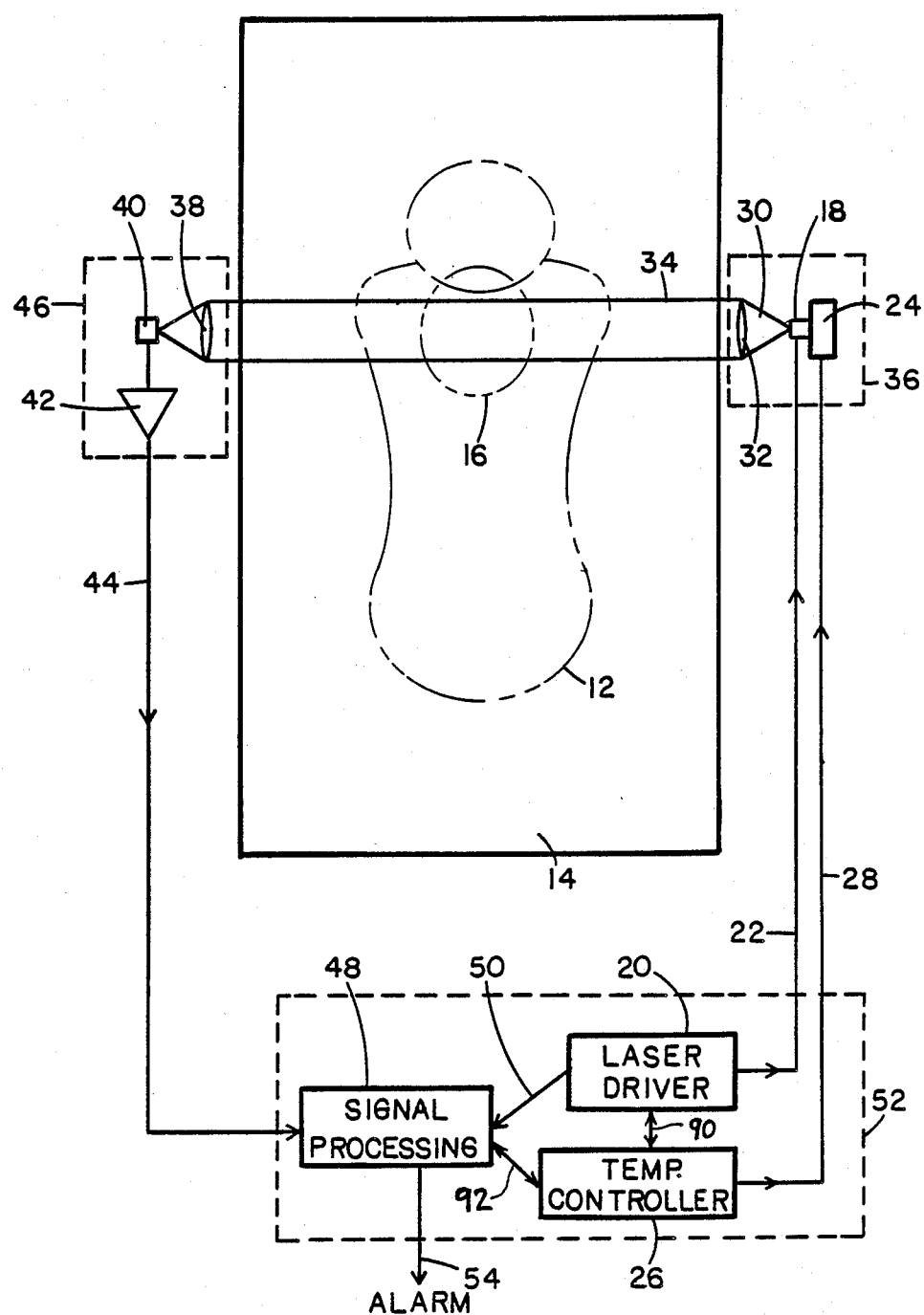
FIG. 1 is a diagram showing the major components of the system in a preferred embodiment.

Turning now to the drawings, in which like parts are denoted by the same reference numeral throughout, there is shown in FIG. 1 an apparatus for detecting apnea of a patient 12 who is lying in a bed 14. As the patient breaths, the air that he exhales is blown into a volume of space 16 that is located in front of the patient in a direction loosely corresponding to the direction of the patient's nasal passages, or his mouth if the patient is breathing through his mouth.

The gases exhaled by the patient expand and diffuse into the surrounding air, and eventually become indistinguishable from the surrounding air. In addition, air currents caused by the movement of persons or by the air conditioning system further promote the diffusion of the exhaled gases into the surrounding air. At any particular time, there is an imaginary envelope separating the gases that are sufficiently concentrated to be detectable from the surrounding air, and the space 16 is bounded by that envelope. In accordance with the present invention, an active source of radiation is provided. In the preferred embodiment of FIG. 1, the active source is a laser diode 18 that is powered by the laser driver circuit 20 through the line 22. In the preferred embodiment, a InGaAsP laser diode is used, and it provides radiation of wavelength in the vicinity of 1.58 microns. This wavelength closely matches one or more of the very narrow vibration-rotation lines that make up the strong absorption band of $CO_2$ in the vicinity of 1.58 microns, and therefore one would expect the transmission of this radiation through carbon dioxide to be related to the concentration of the carbon dioxide.

The InGaAsP laser diode is preferably temperature controlled for fine-tuning, and such control can be achieved by mounting the laser diode 18 on a thermoelectric cooler 24 for both cooling and heating. The thermoelectric cooler is powered by the temperature controller 26 via the line 28. Proper operation of the diode laser as the coherent source requires feedback to the temperature controller 26 of FIG. 1 from both the laser driver via the line 90 and from the signal processing circuit via the line 92. Such feedback control systems are well-known in the art and will not be described in detail here.

The laser diode 18 emits its radiation in a diverging bundle 30 that is collected by the lens 32 and formed into a collimated beam 34 by the lens 32. For convenience, the laser diode 18, the thermoelectric cooler 24 and the lens 32 are packaged in a small enclosure 36 that is attached to the side of the bed 14 or supported on a stand adjacent the bed.

The collimated beam 34 traverses the bed 14 and is directed by the lens 32 to pass through the space 16 into which the patient exhales. After passing through that space, the beam is intercepted and collected by the lens 38 which focuses the radiation onto the detector 40. In the preferred embodiment, a germanium photodiode is used, and in an alternative embodiment a InGaAsP detector is used. The detector 40 generates an electrical signal that is related to the radiant power falling on it, and that electrical signal is strengthened by the preamplifier 42.

In the preferred embodiment, the lens 38, the detector 40, and the preamplifier 42 are packaged into the enclosure 46 which is attached to the side of the bed 14 or supported on a stand adjacent the bed. The strengthened signal on the line 44 is applied to the signal processing circuit 48 which will be described in greater detail below. The signal processing circuit 48 examines the electrical signal 44 to determine whether it varies in a manner that indicates the patient is breathing. If such variations are not found to be present, the signal processing circuit 48 provides an alarm signal on the line 54.

In the preferred embodiment, synchronous detection is employed, and the laser driver circuit 20 provides a synchronizing signal on the line 50 to the signal processing circuit 48.

In the preferred embodiment, the laser driver 20, the temperature controller 26, and the signal processing circuit 48 are packaged in the enclosure 52, which may conveniently be located at the foot of the bed or under the bed.

Figure 2:
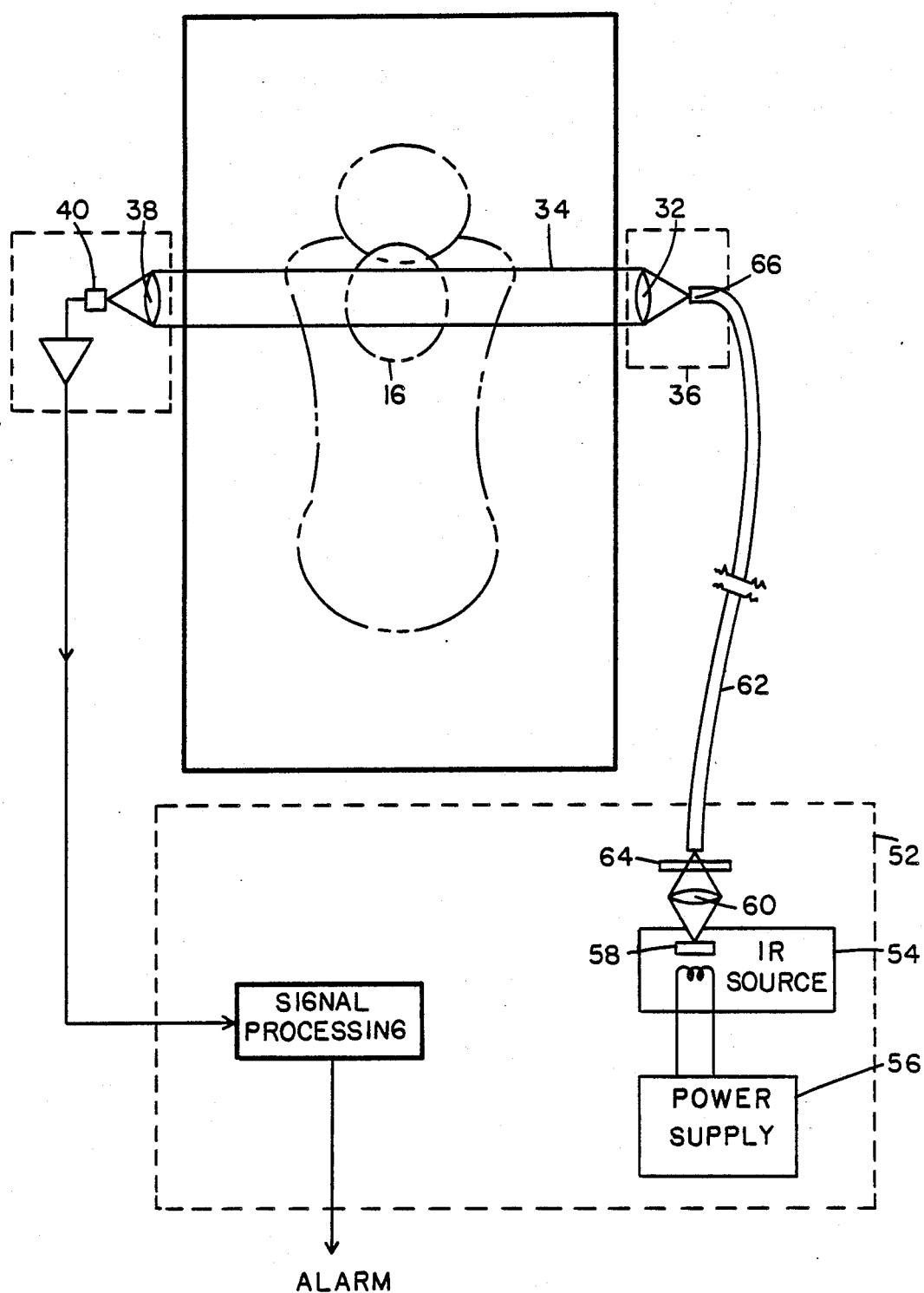
FIG. 2 is a diagram showing the major components of an alternative embodiment of the system.
Figure 3:
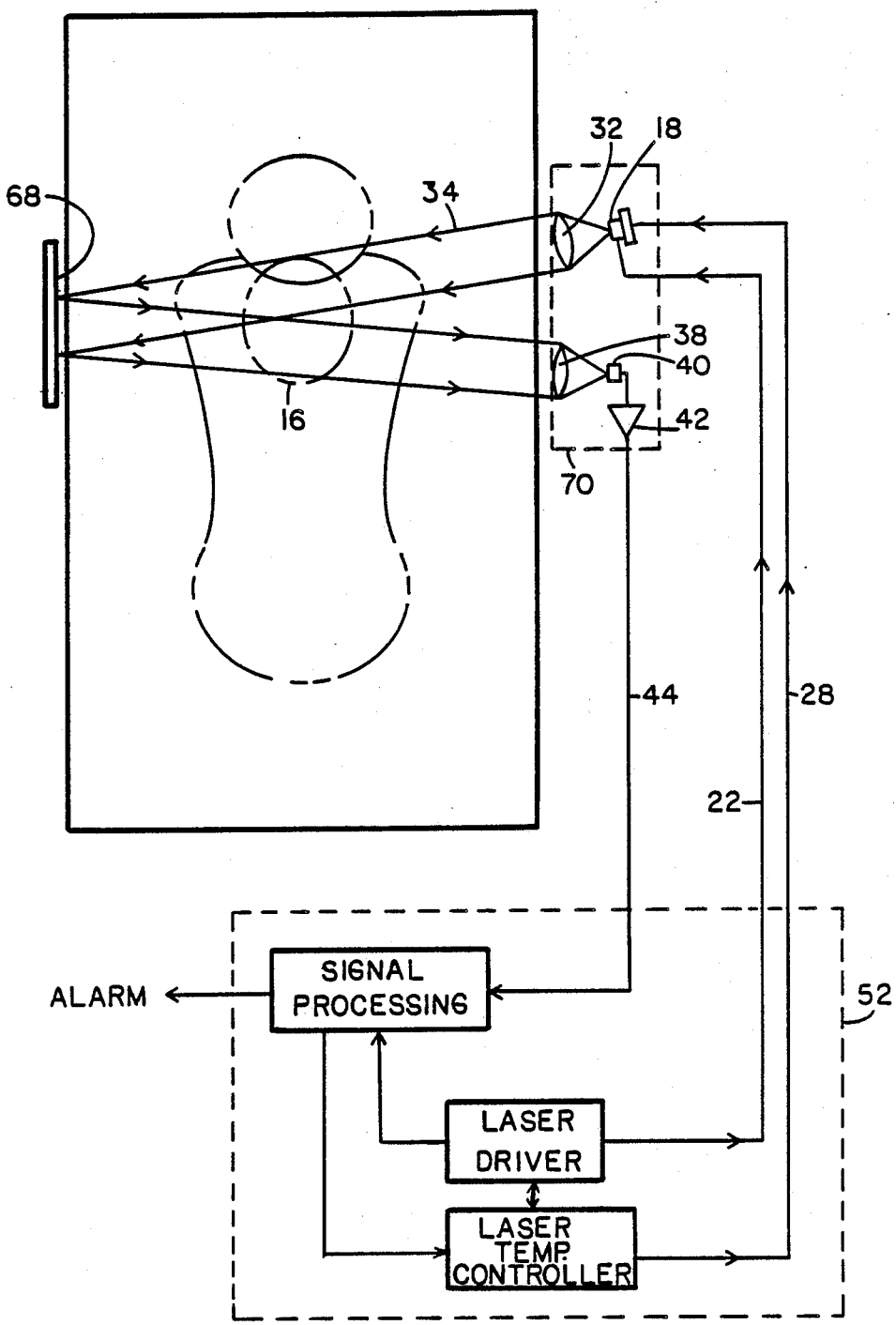
FIG. 3 is a diagram showing the major components of a second alternative embodiment of the system.

In addition to the preferred embodiment shown in FIG. 1, alternative embodiments such as those shown in FIG. 2 and 3 can also be used to advantage. In the alternative embodiment of FIG. 2, a collimated beam of infrared radiation 34 is used to determine the presence of carbon dioxide gas in the space 16 into which the patient exhales. A continuously-emitting source 54 of infrared radiation is used. It includes a heated plate 58 that is maintained at a selected temperature by the power supply 56. Such a source is generally called a quasi-blackbody source. The heated plate 58 emits infrared radiation which is focused by the lens 60 onto the end of an infrared transmitting fiber 62. A chopper 64 is interposed between the lens 60 and the end of the fiber 62 to modulate the radiation.

The fiber 62 conveys the infrared radiation to its other end 66 from which it emerges in a diverging bundle. That bundle is intercepted and formed into the beam 34 by the lens 32.

The embodiment of FIG. 2 has the advantage that the infrared source 54, the chopper 64, and the power supply 56 can be located in the enclosure 52 rather than adjacent the side of the bed, thereby permitting the enclosure 36 to be more compact.

The alternative embodiment shown in FIG. 3 illustrates yet other possibilities. In that embodiment, the beam 34 is directed through the space 16 to a mirror appropriate to the wavelength of the radiation in the beam. The beam is then reflected from the mirror 68 to the lens 38 and passes through the space 16 a second time. Several advantages are gained by the alternative embodiment of FIG. 3. First, the beam 34 passes twice through the space 16, so that absorption by carbon dioxide in that space is accentuated by the increased path length. Second, because the beam reflected by the mirror 68 is displaced from the incident beam, the area probed by the beam is greater than where the beam passes only once across the bed. A third advantage is that the enclosure 46 of FIG. 1 is replaced by the mirror 68 of FIG. 3, permitting the lines 22, 28, and 44 to be bound together in a single cable that connects the enclosure 70 with the enclosure 52.

In a further embodiment of the invention, the laser diode is a AlGaAs laser diode, which radiates at a wavelength of 0.762 microns. In this embodiment, the detector 40 is a silicon photodiode, although in a further variation, a germanium photodiode may also be used. Except for these changes, the system of this embodiment is identical to the system shown in FIG. 1. However, the alternative laser diode and detector enable the system to detect varying concentrations of oxygen, rather than carbon dioxide. It is generally known that oxygen makes up about 20.6% of the atmosphere, and that oxygen accounts for only 16% of the exhaled air, the difference being taken up by the human body to sustain metabolic processes.

Figure 4:
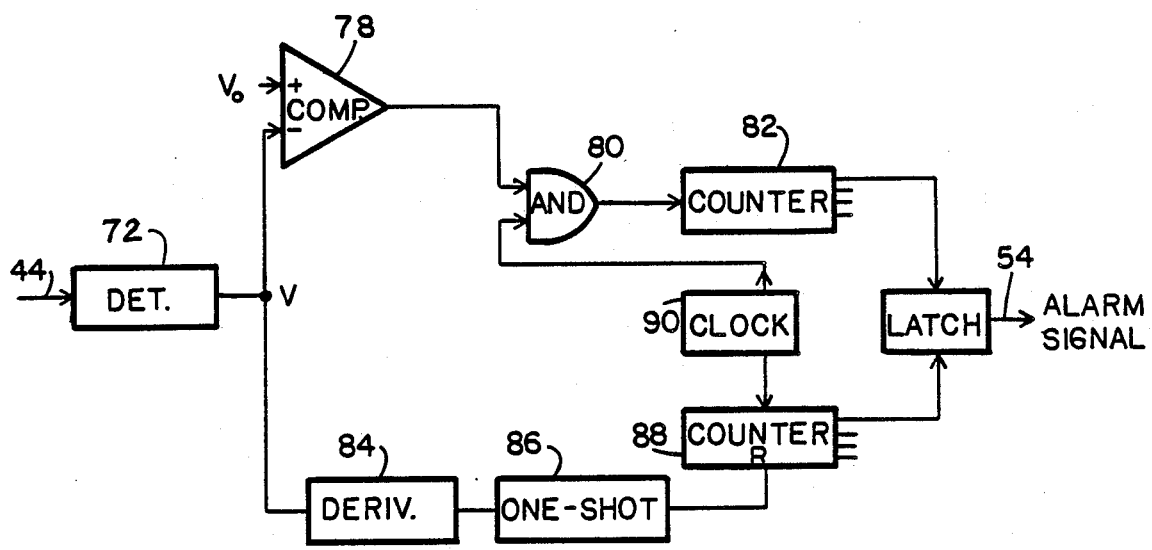
FIG. 4 is an electronic block diagram of the signal processing component of the system in a preferred embodiment; and, FIG. 5 is a graph showing a demodulated voltage waveform as a function of time.

FIG. 4 is a block diagram showing, in a preferred embodiment, the implementation of the signal processing pulsed mode circuit 48. Normally, the laser diode is operated in a pulsed mode, and the signal on the line 44 of FIG. 1 typically consists of a train of voltage pulses. These pulses are demodulated by the detector 72, which produces a relatively slowly varying output V, the magnitude of which indicates the strength of the signal received by the detector 40.

Figure 5:
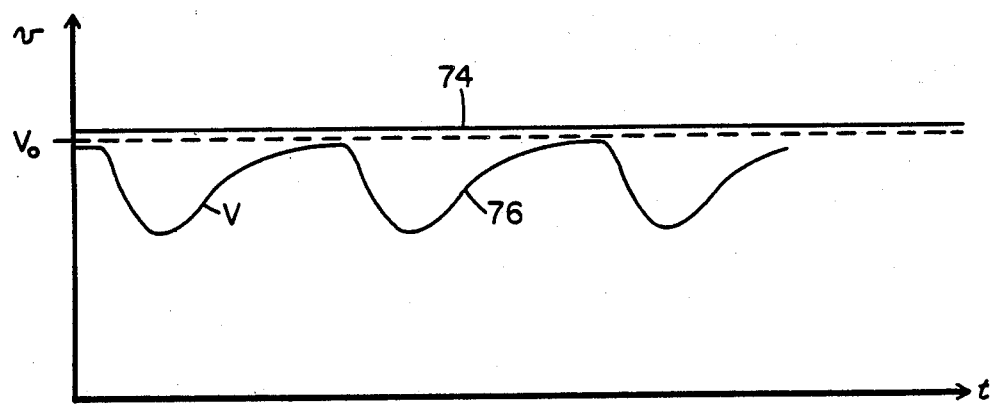

FIG. 5 is a graph showing how the demodulated signal V varies with respect to time in a typical situation. The solid line 74 is the voltage level that would be observed if the patient were not present. The curve 76 shows the fluctuations in the detected voltage as the patient breaths. During the exhalations, the carbon dioxide content in the space 16 increases, causing increased absorption and a resulting decrease in the radiation reaching the radiation detector 40. The downwardly sloping portions of the curve are associated with exhalations, while the upwardly sloping portions of the curve reflect the diffusion of the carbon dioxide between exhalations.

In the preferred embodiment, both the amplitude of the variations in the voltage V and the frequency of the downwardly sloping segments of the curve 76 are monitored, using the circuit of FIG. 4.

In that circuit, the voltage V is applied to the negative terminal of the comparator 78. A constant voltage $V_0$, slightly less than the level 74 of FIG. 5, is applied to the positive terminal of the comparator 78. The output of the comparator 78 remains in a LOW state unless V exceeds a level $V_0$ which was chosen to be slightly less than the level 74 of FIG. 5. The output of the comparator is applied to the AND gate 80, along with clock pulses. Thus, the counter 82 will count the clock pulses only so long as V exceeds $V_0$. If this condition prevails for more than a preset time, an alarm signal will be generated by the counter on the line 54. This illustrates the amplitude criterion for generating the alarm signal. It is based on the idea that if the magnitude of the variations in the curve 76 remains small for a prolonged period, then the patient is not breathing, or has moved to a position in which the space 16 is no longer traversed by the beam 34, and consequently the patient is not under surveillence. In either event, the alarm should be generated.

As also seen in FIG. 4, the voltage V is also applied to the differentiating circuit 84 which produces an output that represents the derivative of V with respect to time. The output of the differentiating circuit 84 is applied to the one-shot multivibrator 86, which responses to a negative-going input by producing a single pulse of preset duration that is applied to the RESET input of the counter 88. This serves to reset the counter at the beginning of each exhalation. Thereafter, the clock 90 continuously supplies pulses which are counted by the counter 88. If there is no second exhalation within a preset time, the count on the counter 88 reaches and exceeds a preset value thereby causing an alarm signal to be generated on the line 54. This portion of the signal processing circuit implements the frequency criterion by providing that if a second exhalation does not follow a first exhalation within a preset interval, the alarm should be sounded because either the patient has stopped breathing or has moved to a position at which he is no longer under surveillance.

In alternative embodiments, either of the two criteria included within the preferred embodiment of FIG. 4 could be used separately. It should also be clear that other electronic components could be used to implement the alarm criteria, but those are considered to be within the scope and spirit of the present invention.

If, instead of carbon dioxide, oxygen is used as the absorbing gas, then the vertical axis in FIG. 5 must be reversed and some polarity changes would have to be made to FIG. 4. These changes are regarded as readily apparent.

Thus, there has been described a preferred embodiment and several alternative embodiments of a system for using a controlled active source of radiation to produce a beam of radiation that is directed through the space into which the patient exhales for the purpose of detecting changes in the concentration of carbon dioxide or of oxygen in the exhaled gases. This system is capable of far greater sensitivity than passive systems previously known in the art and should therefore lead to more widespread use of apnea warning systems with a concomitant decrease in the death rate from that cause.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. Apparatus for detecting apnea of a sleeping patient without the need to confine the patient under a hood or to require the patient to breathe through a tube or a mask, said apparatus comprising:

a semiconductor laser diode means for emitting substantially monochromatic coherent radiation in the 0.762 micron absorption band of oxygen;

first means located so as to collect some of the radiation emitted by said semiconductor laser diode, for forming it into a collimated beam of radiation and for directing the collimated beam to pass through a space into which the patient is exhaling;

second means located so as to intercept and collect the collimated beam after it has passed through the space into which the patient is exhaling;

third means located so as to detect the collected radiation and to produce an electrical signal representative of the quantity of radiation collected and, fourth means electrically connected to said third means for analyzing the electrical signal to determine whether it undergoes variations of appropriate magnitude and frequency to indicate satisfactory breathing by the patient, and for producing an output signal when satisfactory breathing is not indicated.

2. The apparatus of claim 1 wherein said first means further include fiber optics.

3. The apparatus of claim 1 wherein said first means further include at least one mirror for intercepting the collimated beam after it has passed through the space into which the patient is exhaling and for redirecting the collimated beam back through that space.

4. The apparatus of claim 1 wherein said semiconductor laser diode means is an AlGaAs laser and wherein said third means includes a silicon photodiode detector.

5. The apparatus of claim 1 wherein said semiconductor laser diode means is an AlGaAs laser and wherein said third means includes a germanium photodiode detector.

6. Apparatus for detecting apnea of a sleeping patient without the need to confine the patient under a hood or to require the patient to breathe through a tube or a mask, said apparatus comprising:

a semiconductor laser diode means for emitting substantially monochromatic coherent radiation in the 1.58 micron absorption band of carbon dioxide;

first means located so as to collect some of the radiation emitted by said semiconductor laser diode, for forming it into a collimated beam of radiation and for directing the collimated beam to pass through a space into which the patient is exhaling;

second means located so as to intercept and collect the collimated beam after it has passed through the space into which the patient is exhaling;

third means located so s to detect the collected radiation and to produce an electrical signal representative of the quantity of radiation collected; and, fourth means electrically connected to said third means for analyzing the electrical signal to determine whether it undergoes variations of appropriate magnitude and frequency to indicate satisfactory breathing by the patient, and for producing an output signal when satisfactory breathing is not indicated.

7. The apparatus of claim 6 wherein said first means further include fiber optics.

8. The apparatus of claim 6 wherein said first means further include at least one mirror for intercepting the collimated beam after it has passed through the space into which the patient is exhaling and for redirecting the collimated beam back through that space.

9. The apparatus of claim 6 wherein said semiconductor laser diode means is an InGaAsP laser and wherein said third means includes a germanium photodiode detector.

10. The apparatus of claim 6 wherein said semiconductor laser diode means is an InGaAsP laser and wherein said third means includes an InGaAsP photodiode detector.

* * * * *